(12) United States Patent
Belur et al.

(10) Patent No.: US 12,390,564 B2
(45) Date of Patent: Aug. 19, 2025

(54) DIALYSIS SYSTEM HAVING ENHANCED VALVE FEATURES

(71) Applicants: BAXTER INTERNATIONAL INC., Deerfield, IL (US); BAXTER HEALTHCARE SA, Glattpark (CH)

(72) Inventors: Shanthakumar Shashanka Jain Belur, Karnataka (IN); Anoop Thirumattathil Ashokan, Karnataka (IN); Harakabhavi Mutt Vinayaka, Karnataka (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/867,141

(22) PCT Filed: May 3, 2023

(86) PCT No.: PCT/US2023/020825
§ 371 (c)(1),
(2) Date: Nov. 19, 2024

(87) PCT Pub. No.: WO2023/224806
PCT Pub. Date: Nov. 23, 2023

(65) Prior Publication Data
US 2025/0170312 A1    May 29, 2025

(30) Foreign Application Priority Data
May 19, 2022 (IN) .............. 202241028982

(51) Int. Cl.
*A61M 1/14* (2006.01)
*A61M 1/28* (2006.01)
*A61M 39/28* (2006.01)

(52) U.S. Cl.
CPC ............ *A61M 1/1565* (2022.05); *A61M 1/14* (2013.01); *A61M 1/154* (2022.05); *A61M 1/28* (2013.01);
(Continued)

(58) Field of Classification Search
CPC ...... A61M 1/14; A61M 1/154; A61M 1/1565; A61M 1/28; A61M 39/28;
(Continued)

(56) References Cited

FOREIGN PATENT DOCUMENTS

| EP | 0659444 | 6/1995 |
|---|---|---|
| WO | 2022031504 | 2/2022 |
| WO | 2022187021 | 9/2022 |

OTHER PUBLICATIONS

International Search Report—PCTUS2023/020825 dated Jul. 7, 2023—4 pages.
Written Opinion—PCTUS2023/020825 dated Jul. 7, 2023—pp. 9 pages.

*Primary Examiner* — John Kim
(74) *Attorney, Agent, or Firm* — K&L Gates LLP

(57) ABSTRACT

A medical fluid system includes a medical fluid pump configured to pump a medical fluid; a tube through which medical fluid pumped by the medical fluid pump flows; a pinch valve positioned and arranged to occlude the tube to prevent medical fluid from flowing through the tube, the pinch valve including a motor; a current sensor positioned and arranged to sense a current drawn by the motor of the pinch valve; and a control unit operable with the current sensor to monitor the current drawn by the motor while the motor is causing the pinch valve to occlude the tube, the control unit configured to stop the motor when the monitored current indicates an occlusion of the tube.

15 Claims, 9 Drawing Sheets

(52) U.S. Cl.
CPC ..... *A61M 39/28* (2013.01); *A61M 2202/0007* (2013.01); *A61M 2202/04* (2013.01); *A61M 2205/103* (2013.01); *A61M 2205/128* (2013.01); *A61M 2205/15* (2013.01); *A61M 2205/3317* (2013.01); *A61M 2205/3327* (2013.01); *A61M 2205/3331* (2013.01); *A61M 2205/3365* (2013.01); *A61M 2205/50* (2013.01)

(58) Field of Classification Search
CPC ...... A61M 2202/0007; A61M 2202/04; A61M 2205/103; A61M 2205/128; A61M 2205/15; A61M 2205/3317; A61M 2205/3327; A61M 2205/3331; A61M 2205/3365; A61M 2205/50
See application file for complete search history.

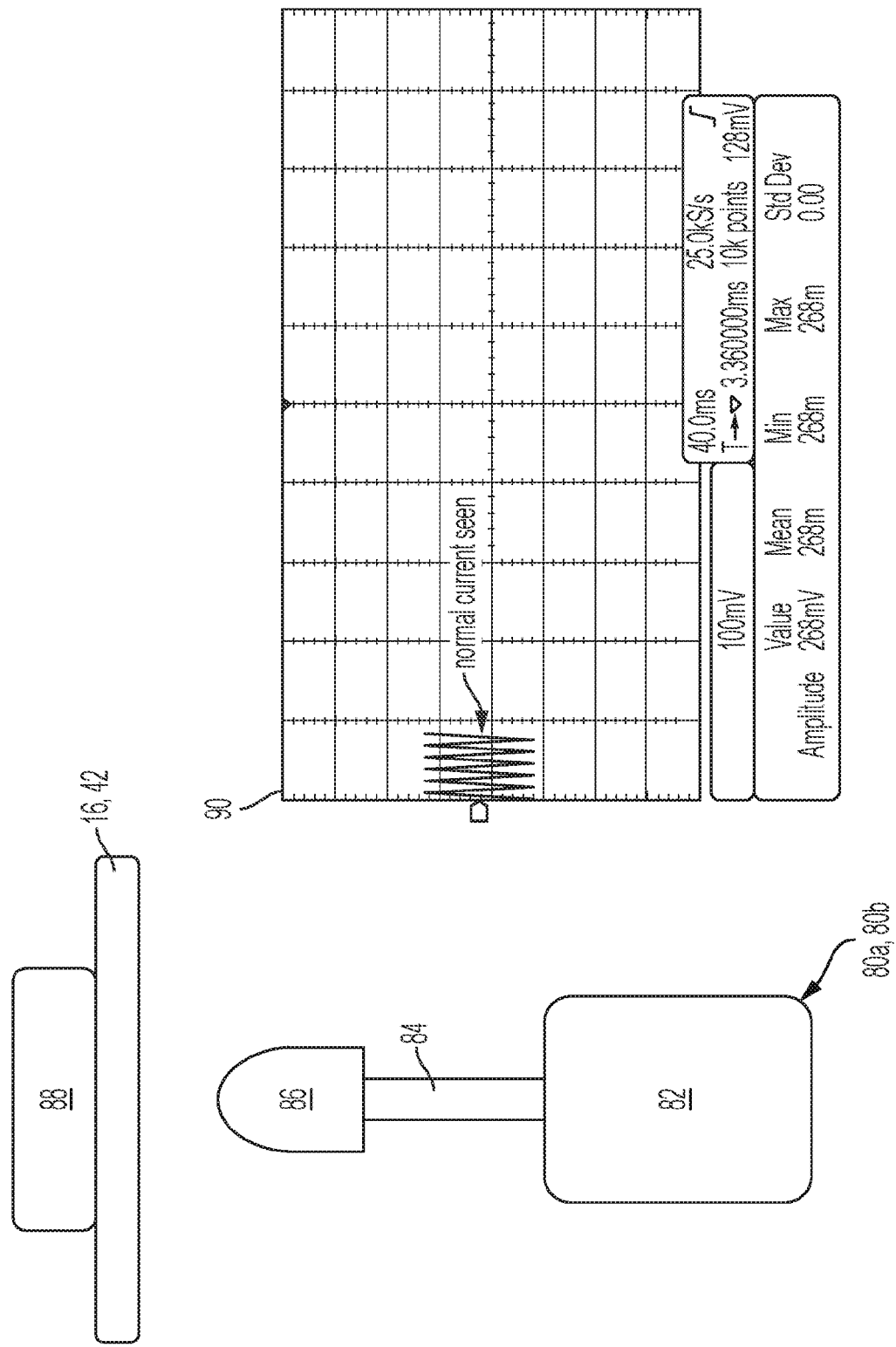

DIALYSIS SYSTEM HAVING ENHANCED VALVE FEATURES

PRIORITY CLAIM

The present application is a national phase entry of PCT Patent Application No. PCT/US2023/020825, filed on May 3, 2023, which claims priority to and the benefit of Indian Provisional Application No. 202241028982, filed on May 19, 2022, the entire contents of which are hereby incorporated by reference.

BACKGROUND

The present disclosure relates generally to medical fluid treatments and in particular to dialysis fluid treatments that require fluid heating.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Each of the above-identified dialysis modalities, except for CAPD (which typically does not involve machinery), uses automated valves to control whether dialysis fluid, blood or other fluid is able to flow or not flow. The valves also control the direction of fluid flow, such as where the fluid comes from or the destination to which the fluid flows. Different types of valves are used in dialysis system. One type of valve is used typically with a disposable cassette having a hard plastic part defining fluid flow paths and valve seats and one or more flexible membrane covering one or more side of the hard plastic part. The disposable cassette is typically loaded into a dialysis machine or cycler, which is able to close designated parts of the one or more plastic sheet against the valve seats to block fluid flow and to force or allow the plastic to move away from the valve seats to allow fluid flow.

Another type of automated valve is a pinch valve that instead pinches closed a tube carrying the dialysis fluid, blood or other fluid to block fluid flow. There are generally two types of pinch valves, solenoid pinch valves and motorized pinch valves. Motorized pinch valves need to be configured for a particular tubing diameter and a particular tubing wall thickness. Tubing diameters and wall thicknesses are not always consistent for different sets of tubing, and the tubing wall thickness may further vary over time due to wear and tear via repeated pinching.

An improved way to operate motorized pinch valves is needed accordingly.

SUMMARY

The present disclosure sets forth a motorized valve for a medical fluid system, such as an automated peritoneal dialysis ("PD") system, which improves the usability of the valve. While the present system is described primarily in connection with PD, the improved motorized valve operation of the present disclosure applies to machines used for any dialysis modality described herein, such as online HD, HF, HDF, and acute HD, HF, HDF. The improved motorized valve operation of the present disclosure also applies to any medical fluid system in which a treatment fluid flow, or a patient fluid flow, is controlled via one or more valve.

In a PD example, the system includes a PD machine or cycler. The PD machine is described herein primarily as having a pneumatically driven PD fluid pump and the electromechanically actuated motorized pinch valves of the present disclosure. Alternatively, however, the PD fluid pump may also be electromechanically driven, e.g., be a piston, gear, peristaltic or centrifugal pump. The PD machine or cycler is in one embodiment capable of delivering fresh, heated PD fluid to the patient at, for example, 14 kPa (2.0 psig) or higher. The PD machine is capable of removing used PD fluid or effluent from the patient at, for example, −9 kPa (−1.3 psig) or an even greater negative pressure. Fresh PD fluid delivered to the patient may be first heated to a body fluid temperature, e.g., 37° C.

The PD machine or cycler of the present system operates with motorized pinch valves under control of a control unit. The control unit may include one or more current sensor that operates with a processor and/or memory of the control unit. A dedicated current sensor may be provided for each motorized pinch valve, allowing completely independent actuation of each of the valves. Or, one or more current sensor may be provided for multiple motorized pinch valves, e.g., where it is assured that the timing of the initiation of the actuation of the multiple pinch valves will not overlap. The current sensors may be provided on a control board of the control unit or be located alternatively within the pinch valves, which may include a rotary nut motor under control of control unit. The rotary nut motor may be a stepper motor. The rotary nut located within rotary nut motor is translationally fixed, such that its rotation causes a threaded shaft to be threaded through the rotary nut so to translate in an accurate manner in both valve closing and valve opening directions. The end of threaded shaft that contacts the tube includes a rounded head or wedge that allows the tubes or lines to be occluded without damaging the tubing. The pinch valves also include a stop against which the rounded head or wedge compresses the tubes.

The rotary nut motor rotates the rotary nut in a first direction, e.g., clockwise, to cause threaded shaft and rounded head to translate in a first direction towards the stop to occlude a tube. The rotary nut motor rotates the rotary nut in a second direction, e.g., counterclockwise, to cause the threaded shaft and the rounded head to translate in a second direction away from the stop, allowing medical fluid to flow through the tube.

Prior art control of the motorized pinch valves can be deficient when the shaft is moved a set distance expected to fully occlude the tube fails to do so because the tube wall thickness at the point of contact has thinned due to repeated occlusion, for example. A corresponding fluid leak occurs. Also, if the diameter of the tube and/or tube wall thickness is/are different than what is expected for the set translation distance, a leak may occur even if the tube wall thickness has not been worn or thinned.

The present method solves the above problems by monitoring the output of the motorized valves' corresponding current sensor during tube occlusion. The control unit of the machine or cycler determines if the output from the current sensor shows a spike or characteristic change indicating that the tube has been fully occluded and that threaded shaft and rounded head are pushing against the stop, which forces the rotary nut motor into a stalled condition. That is, the rotary nut motor will draw more current in an end-of-travel, fully occluded state, in an attempt to keep the rotary nut rotating. The additional current draw is detected by the current sensor. If the output from current sensor does not show a spike or characteristic change indicating that the tube has been fully occluded, then control unit continues to monitor the current sensor and to cause the rotary nut motor to rotate, further translating the threaded shaft and the rounded head. If the output from the current sensor does show a spike or characteristic change indicating that the tube has been fully occluded, then control unit depowers the rotary nut motor.

In light of the disclosure set forth herein, and without limiting the disclosure in any way, in a first aspect of the present disclosure, which may be combined with any other aspect, or portion thereof, a medical fluid system includes a medical fluid pump configured to pump a medical fluid; a tube through which medical fluid pumped by the medical fluid pump flows; a pinch valve positioned and arranged to occlude the tube to prevent medical fluid from flowing through the tube, the pinch valve including a motor; a current sensor positioned and arranged to sense a current drawn by the motor of the pinch valve; and a control unit operable with the current sensor to monitor the current drawn by the motor while the motor is causing the pinch valve to occlude the tube, the control unit configured to stop the motor when the monitored current indicates an occlusion of the tube.

In a second aspect of the present disclosure, which may be combined with any other aspect, or portion thereof, the monitored current increases to indicate the occlusion of the tube.

In a third aspect of the present disclosure, which may be combined with any other aspect, or portion thereof, the current sensor is provided with the control unit or the pinch valve.

In a fourth aspect of the present disclosure, which may be combined with any other aspect, or portion thereof, the current sensor is configured to sense the current drawn by multiple motors of multiple pinch valves.

In a fifth aspect of the present disclosure, which may be combined with any other aspect, or portion thereof, the pinch valve includes a shaft driven by the motor.

In a sixth aspect of the present disclosure, which may be combined with any other aspect, or portion thereof, the motor is a rotary nut motor and the shaft is a threaded shaft.

In a seventh aspect of the present disclosure, which may be combined with any other aspect, or portion thereof, the shaft includes a head that contacts the tube, the valve further including a stop against which the head occludes the tube.

In an eighth aspect of the present disclosure, which may be combined with any other aspect, or portion thereof, the tube is a first tube and the pinch valve is a first pinch valve, and wherein the control unit is operable with the current sensor or a second current sensor to monitor the current drawn by a second motor of a second pinch valve while the second motor is causing the second pinch valve to occlude the second tube, the control unit further configured to stop the second motor when the monitored current indicates an occlusion of the second tube.

In a ninth aspect of the present disclosure, which may be combined with any other aspect, or portion thereof, the control unit is further configured to operate the motor in an opposite direction, without monitoring the current drawn by the motor, to allow medical fluid to flow through the tube.

In a tenth aspect of the present disclosure, which may be combined with any other aspect, or portion thereof, the tube is disposable or reusable.

In an eleventh aspect of the present disclosure, which may be combined with any other aspect, or portion thereof, the control unit is configured to wait momentarily after the monitored current initially indicates the occlusion of the tube before stopping the motor.

In a twelfth aspect of the present disclosure, which may be combined with any other aspect, or portion thereof, a medical fluid system includes a medical fluid pump configured to pump a medical fluid; a tube through which medical fluid pumped by the medical fluid pump flows; a pinch valve positioned and arranged to occlude the tube to prevent medical fluid from flowing through the tube, the pinch valve including a motor; a sensor positioned and arranged to sense a characteristic change associated with the motor of the pinch valve when the tube is occluded; and a control unit operable with the sensor, the control unit configured to stop the motor when the characteristic change is sensed.

In a thirteenth aspect of the present disclosure, which may be combined with any other aspect, or portion thereof, the sensor is a current sensor, a resistance sensor, a hall effect sensor, or a current transformer.

In a fourteenth aspect of the present disclosure, which may be combined with any other aspect, or portion thereof, the characteristic change is a characteristic increase in current drawn by the motor.

In a fifteenth aspect of the present disclosure, which may be combined with any other aspect, or portion thereof, the control unit is configured to wait momentarily after the characteristic change is sensed before stopping the motor.

In a sixteenth aspect of the present disclosure, which may be combined with any other aspect, or portion thereof, a method for controlling a motorized pinch valve for medical fluid flow includes (i) powering a motor of the motorized pinch valve such that a shaft of the motorized pinch valve move in a tube occlusion direction; (ii) monitoring a sensor output indicative of a current drawn by the motor while powering the motor; (iii) if a change in the sensor output characteristic of an occlusion of the tube is not detected, returning to (i); and (iv) if a change in the sensor output characteristic of the occlusion of the tube is detected, depowering the motor.

In a seventeenth aspect of the present disclosure, which may be combined with any other aspect, or portion thereof, the sensor is a current sensor.

In an eighteenth aspect of the present disclosure, which may be combined with any other aspect, or portion thereof, the output characteristic of the occlusion of the tube includes an increase in current drawn by the motor.

In a nineteenth aspect of the present disclosure, which may be combined with any other aspect, or portion thereof, wherein in (iv) the change in the sensor output characteristic of the occlusion of the tube is detected for a period of time sufficient to ensure that the change is due to the occlusion of the tube and not some other anomaly.

In a twentieth aspect of the present disclosure, which may be combined with any other aspect, or portion thereof, the change in the sensor output characteristic of the occlusion of the tube is detected regardless of tube wear, tube softness or tube manufacturing tolerances.

In a twenty-first aspect of the present disclosure, which may be combined with any other aspect, or portion thereof, any of the features, functionality and alternatives described in connection with any one or more of FIGS. 1 to 6D may be combined with any of the features, functionality and alternatives described in connection with any other of FIGS. 1 to 6D.

In light of the above aspects and present disclosure set forth herein, it is an advantage of the present disclosure to provide a medical fluid system having improved motorized pinch valve operation.

It is another advantage of the present disclosure to provide a medical fluid system having improved motorized pinch valve flexibility, wherein the valves may operate with multiple different diameters/wall thicknesses of tubing and be able to compensate for tubing wall thickness variations.

It is a further advantage of the present disclosure to provide a medical fluid system having simplified motorized pinch valves.

Moreover, it is an advantage of the present disclosure to provide a medical fluid system having compact motorized pinch valves.

It is yet another advantage of the present disclosure to provide a medical fluid system having effective leak proof tube pinching irrespective of tube thickness variation and wear due to repeated pinches.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIGS. 6A to 6D are schematic elevation views illustrating the structure and methodology of the present disclosure for occluding a flexible tube using a motorized pinch valve.

DETAILED DESCRIPTION

Figure 1:
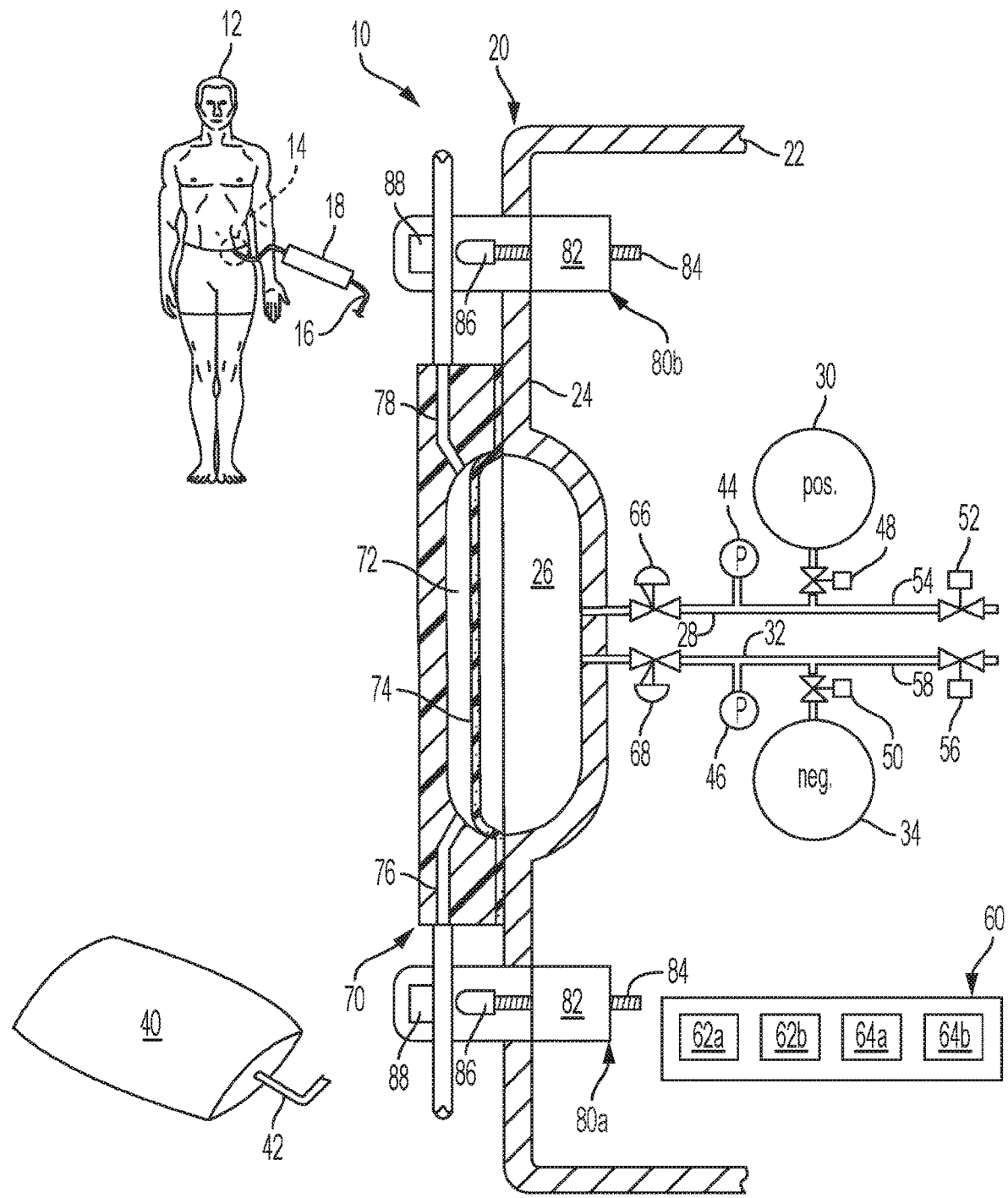
FIG. 1 is a sectioned schematic view of one embodiment for an APD system having the motorized pinch valve operation of the present disclosure.

Referring now to the drawings and in particular to FIG. 1, an example system 10 including the motorized pinch valve operation of the present disclosure is illustrated. System 10 includes a dialysis machine 20, such as an automated peritoneal dialysis ("PD") machine, operating a medical fluid handling device 70, such as a dialysis fluid cassette. While present system 10 is described primarily in connection with PD, the improved motorized valve operation of the present disclosure applies to machines used for any dialysis modality described herein, such as online HD, HF, HDF, and acute HD, HF, HDF. The improved motorized valve operation of the present disclosure also applies to any medical fluid system in which a treatment fluid flow, or a patient fluid flow, is controlled via one or more valve.

PD machine 20 in the illustrated embodiment includes a housing 22 defining a pump interface 24 having a pump actuator or pump actuation area 26 for actuating medical fluid handling device 70. Pump actuation area 26 in the illustrated embodiment is actuated pneumatically via a positive pneumatic line 28 extending from a positive pneumatic source 30 to perform a pump-out or discharge stroke, e.g., to push (i) fresh, heated dialysis fluid to a peritoneal cavity 14 of patient 12 via a patient line 16 and patient transfer set 18, for example, at 14 kPa (2.0 psig) or higher, (ii) fresh dialysis fluid at a higher system pressure to a heating container (not illustrated) to be heated to body temperature, e.g., 37° C., by a dialysis fluid heater (not illustrated), or (iii) used dialysis fluid at a higher system pressure to a drain. Pump actuation area 26 in the illustrated embodiment is actuated pneumatically via a negative pneumatic line 32 extending from a negative pneumatic source 34 to perform a pump-in or draw stroke, e.g., to pull (i) fresh dialysis fluid from a dialysis fluid source 40 through a supply line 42 at a higher system pressure, (ii) fresh, heated dialysis fluid from the heating container (not illustrated) at a higher system pressure, or (iii) used dialysis fluid from the peritoneal cavity 14 of patient 12 via patient line 16 and transfer set 18, for example, at −9 kPa (−1.3 psig) or perhaps at a greater negative pressure.

Patient line 16 may be from three to seven meters long, e.g., approximately 4.5 or 6.7 meters, have an inner diameter of, for example, two to four millimeters ("mm"), and a wall thickness of about one mm. Supply line 42 may also have an inner diameter of, for example, two to four mm, and a wall thickness of about one mm. PD machine 20 also provides a pressure sensor 44 for measuring positive pneumatic pressure in positive pneumatic line 28 and a pressure sensor 46 for measuring negative pneumatic pressure in negative pneumatic line 32. PD machine 20 further includes plural electrically operated pneumatic valves, e.g., valves 48, 50, 52 and 56. Pneumatic valve 48 is positioned in positive pneumatic line 28 to selectively allow positive pressure from source 30 to reach pump actuation area 26. Pneumatic valve 50 is positioned in negative pneumatic line 32 to selectively allow negative pressure from source 34 to reach pump actuation area 26. A vent valve 52 is provided in a vent line 54 in communication with positive pneumatic line 28 to selectively vent positive pressure in line 28 and pump actuation area 26 to atmosphere. A second vent valve 56 is provided in a vent line 58 in communication with negative pneumatic line 32 to selectively vent negative pressure in line 32 and pump actuation area 26 to atmosphere. In an alternative embodiment, a single vent valve and line may be provided to vent both positive and negative pressure from pump actuation area 26 to atmosphere.

FIG. 1 further illustrates that PD machine 20 includes a positive pneumatic pressure regulator 66, e.g., a variable orifice valve, located along positive pneumatic line 28, and a negative pressure regulator 68, e.g., a variable orifice valve, located along negative pneumatic line 32. Positive pneumatic pressure regulator 66 sets the positive pneumatic pressure delivered to pump actuation area 26 to a desired and controlled level, which is also the pressure of fresh or used PD fluid pumped out of dialysis fluid cassette 70. Negative pneumatic pressure regulator 68 sets the negative pneumatic pressure drawn at pump actuation area 26 to a desired and controlled level, which is also the pressure of fresh or used PD fluid pumped into dialysis fluid cassette 70. In an alternative embodiment, PD machine 20 may be configured pneumatically such that a single pressure regulator, e.g., variable orifice valve, operates at different times as a positive pneumatic pressure regulator and a negative pneumatic pressure regulator.

Pressure sensors 44 and 46, pneumatic valves 48, 50, 52 and 56, and variable orifice valves or regulators 66 and 68 either output to or are under the control of a control unit 60 of PD machine 20. Control unit 60 in the illustrated embodiment includes one or more processor 62a and one or more memory 62b. Control unit 60 may have any one or more of a master controller, safety controller, video controller, and/or sub- or delegate controller.

In the illustrated embodiment of FIG. 1, medical fluid handling device or disposable cassette 70 is provided with a pump actuation chamber 72 that mates with pump actuation area 26 to form an overall pumping chamber. Medical fluid handling device 70 in the illustrated embodiment includes a flexible membrane, diaphragm or sheet 74, which may be sized to fit pump actuation chamber 72 or be sized to cover a whole side of medical fluid handling device 70 (as illustrated), wherein a portion of the membrane 74 covers pump actuation chamber 72, and wherein such portion may be at least substantially flat or be pre-domed or pre-shaped to fit into one or both pump actuation area 26 and pump actuation chamber 72. Control unit 60 causes negative pressure from source 34 to be applied to flexible membrane 74 to pull the sheet against the wall of pump actuation area 26 to correspondingly pull fresh or used PD fluid into pump actuation chamber 72. To do so, control unit causes valves 48, 52 and 56 to be closed and valve 50 to be open. During the filling of pump actuation chamber 72, pressure sensor 46 measures negative pumping pressure, which is used as feedback in a pressure control routine to set the level of negative pneumatic pressure applied at pump actuation area 26 via negative pressure regulator 68.

Control unit 60 causes positive pressure from source 30 to be applied to flexible membrane 74 to push the sheet against the wall of pump actuation chamber 72 to correspondingly push fresh or used PD fluid from pump actuation chamber

72. To do so, control unit causes valves 50, 52 and 56 to be closed and valve 48 to be open. During the discharge of pump actuation chamber 72, pressure sensor 44 measures positive pumping pressure, which is used as feedback in a pressure control routine to set the level of positive pneumatic pressure applied at pump actuation area 26 via positive pressure regulator 66.

Control unit 60 is able to determine the flowrate of fresh and used PD fluid pumped by PD machine 20 of system 10 in at least one of a plurality of different ways. In one way, the fixed volumes of pump actuation area 26 and pump actuation chamber 72 collectively form a known full stroke volume. Control unit 60 counts the number of full strokes delivered, multiplies the count by the known full stroke volume, and divides the result by the corresponding amount of time needed to perform the number of full strokes delivered to determine a local or current PD fluid flowrate.

Alternatively or additionally, control unit 60 takes before and after fill or discharge stroke pressure measurements and uses an ideal gas law algorithm, as is known in the art, to determine a resulting volume of fresh or used PD fluid pulled into or discharged from pump actuation chamber 72. To do so, PD machine 20 may provide positive and negative known and fixed volume reference chambers (not illustrated), which may be pneumatically connected to positive and negative vent lines 54 and 58, respectively. Control unit 60 may then add consecutive fill or discharge stroke volumes determined by the ideal gas law algorithm and divide the sum by the corresponding amount of time needed to perform the consecutive fill or discharge strokes to determine a local or current PD fluid flowrate. The ideal gas law algorithm method of determining local or current flowrate is advantageous because full stokes of diaphragm or sheet 74 through pump actuation area 26 and pump actuation chamber 72 are not required. Partial strokes may be performed and taken into account in determining local or current flowrate.

It should be appreciated that it is likely that PD machine 20 provides two pump actuation areas 26 and pump actuation chambers 72, which operate in an alternating manner (one filling while the other discharging), so that the flowrate of fresh or used PD fluid is for the most part continuous. Moreover, while FIG. 1 illustrates a pneumatically driven pump actuation area 26 and pump actuation chamber 72, the PD fluid pumping of system 10 may alternatively be electromechanically driven, e.g., via a piston, gear, peristaltic or centrifugal pump.

Regardless of the type of pumping employed by system 10, PD machine 20 includes electromechanical motorized pinch valves 80a, 80b under control of control unit 60 in the illustrated embodiment. As illustrated in FIG. 1, motorized pinch valve 80a is operable with supply line 42, while motorized pinch valve 80b is operable with patient line 16. While FIG. 1 illustrates two motorized pinch valves 80a, 80b, PD machine 20 of system 10 may include additional motorized pinch valves, such as an additional fluid valve for an additional pump actuation chamber 72 (operating in an alternating manner to provide more continuous flow) and additional fluid valves for multiple supply lines 42, a fluid heater line, and/or a drain line, which are not illustrated to simplify FIG. 1.

FIG. 1 illustrates that control unit 60 may further include one or more current sensor 64a, 64b that operates with one or more processor 62a and/or one or more memory 62b. A dedicated current sensor 64a, 64b may be provided for each motorized pinch valve 80a, 80b, respectively, allowing completely independent actuation of each of the valves. Or, one or more current sensor 64a, 64b may be provided for multiple motorized pinch valves 80a, 80b, e.g., where it is assured that the timing of the initiation of the actuation of the pinch valves 80a, 80b does not overlap. While current sensors 64a, 64b are illustrated as being provided with control unit 60, e.g., on a control board of control unit 60, current sensors 64a, 64b may alternatively be located within pinch valves 80a, 80b, respectively.

Figure 2A:
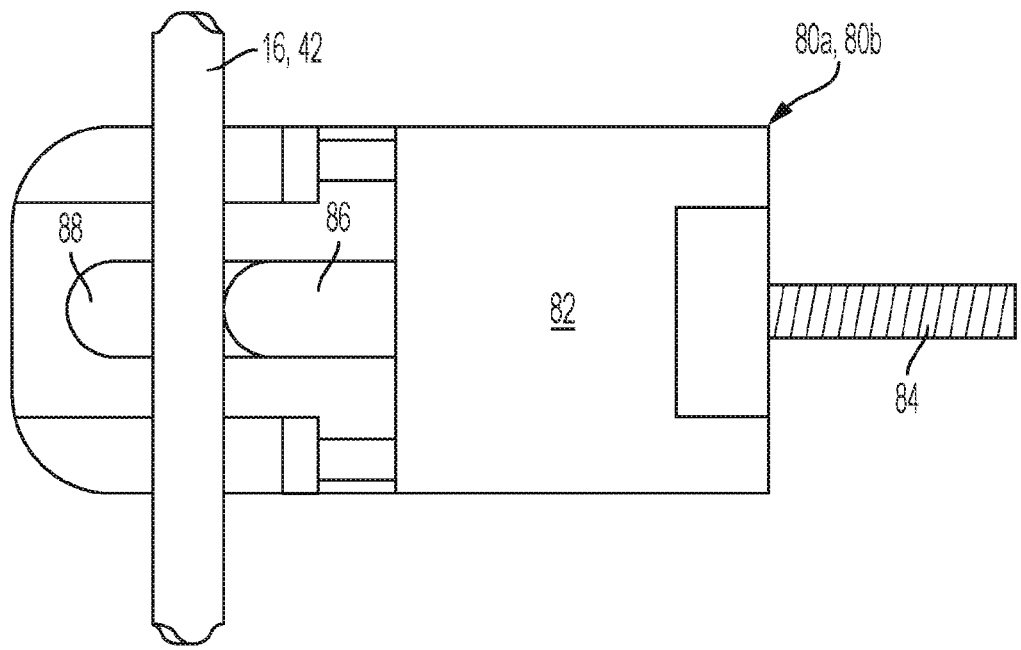
FIGS. 2A and 2B are top and side views, respectively, of one embodiment of a motorized pinch valve of the present disclosure.
Figure 2B:
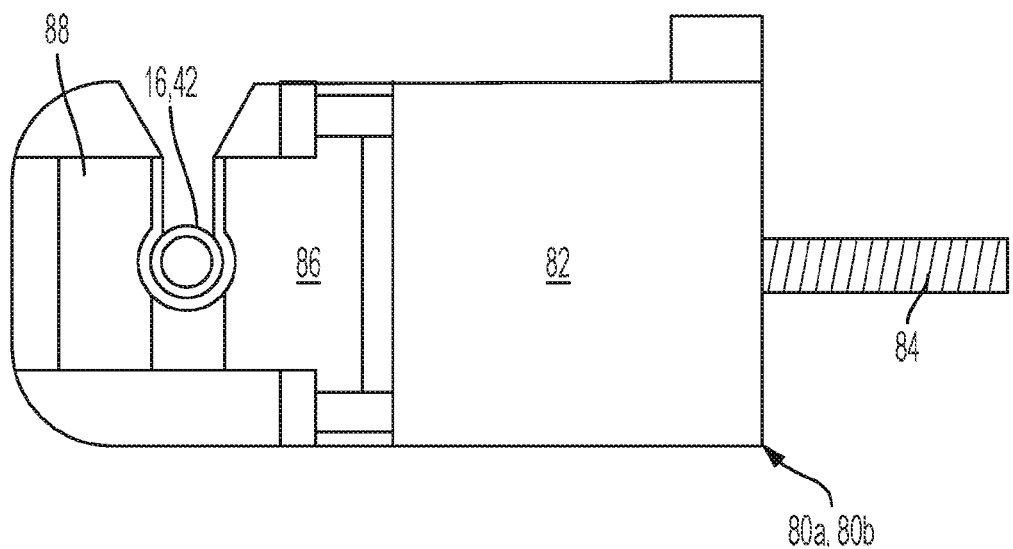

FIGS. 2A and 2B illustrate motorized pinch valves 80a, 80b in more detail. In the illustrated embodiment, motorized pinch valves 80a, 80b each include a rotary nut motor 82 under control of control unit 60. Rotary nut motor 82 may be a stepper motor. The rotary nut located within rotary nut motor 82 is translationally fixed, such that its rotation causes a threaded shaft 84 threaded through the rotary nut to translate in an accurate manner in both valve closing and valve opening directions. The end of threaded shaft 84 that contacts the tube, e.g., patient line 16 or supply line 42 in FIG. 1, is provided with a rounded head or wedge 86 that allows tubes or lines 16, 42 to be occluded without damaging the lines or tubes. Pinch valves 80a, 80b in FIGS. 2A and 2B also include a stop 88 against which rounded head or wedge 86 compresses tubes or lines 16, 42. Rotary nut motor 82 rotates the rotary nut in a first direction, e.g., clockwise, to cause threaded shaft 84 and rounded head 86 to translate in a first direction towards stop 88 to occlude tubes or lines 16, 42. Rotary nut motor 82 rotates the rotary nut in a second direction, e.g., counterclockwise, to cause threaded shaft 84 and rounded head 86 to translate in a second direction away from stop 88 to allow medical fluid flow through tubes or lines 16, 42.

Figure 3:
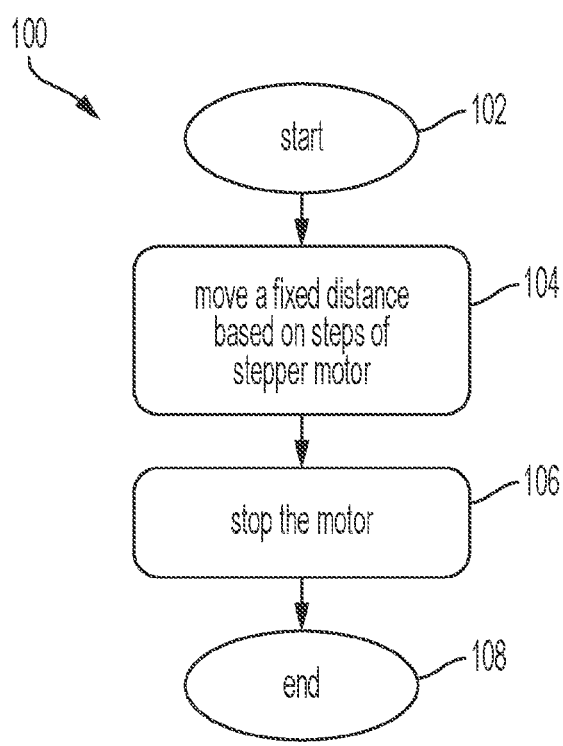
FIG. 3 is a process flow diagram of a prior art method of occluding a flexible tube using a motorized pinch valve.
Figure 4A:
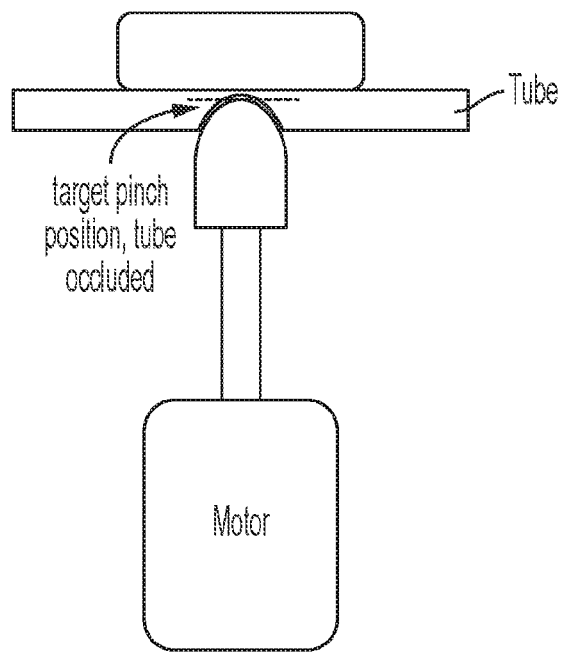
FIGS. 4A and 4B are schematic views illustrating a problem with the prior art operation of motorized pinch valves.
Figure 4B:
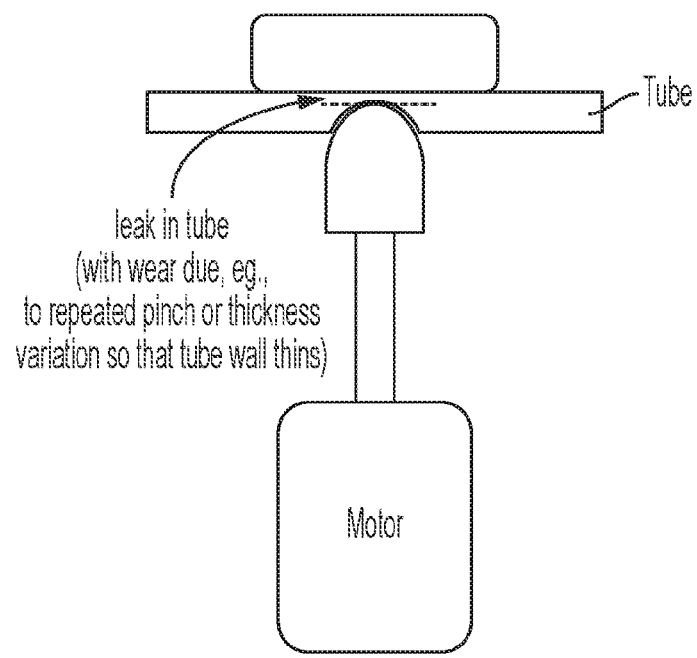

FIG. 3 illustrates a prior art method 100 of occluding a flexible tube using a motorized pinch valve. At oval 102, method 100 begins. At block 104, a rotary nut motor, such as a stepper motor, moves a commanded number of steps that, in combination with the geometry of the threaded shaft, are calculated to create an amount of translational movement of the threaded shaft and rounded head needed to occlude the tubing or lines. The motor is stopped when the commanded number of motor steps have been moved as illustrated at block 106. At oval 108, method 100 ends. FIGS. 4A and 4B illustrate a problem with method 100. When the contacted portion of tubes or lines 16, 42 have their expected thickness as in FIG. 4A, translating the threaded shaft and rounded the calculated fixed distance (to the dotted line) causes tubes or lines 16, 42 to be properly occluded. But when the contacted portion of tubes or lines 16, 42 have thinned, e.g., due to repeated pinching or occlusion or to a manufacturing tolerance in which the tube wall is manufactured so as to be thinner than as specified or intended, as in FIG. 4B, translating the threaded shaft and rounded head the calculated fixed distance (to the dotted line) does not cause tubes or lines 16, 42 to be properly occluded, such that a leak is created.

Figure 5:
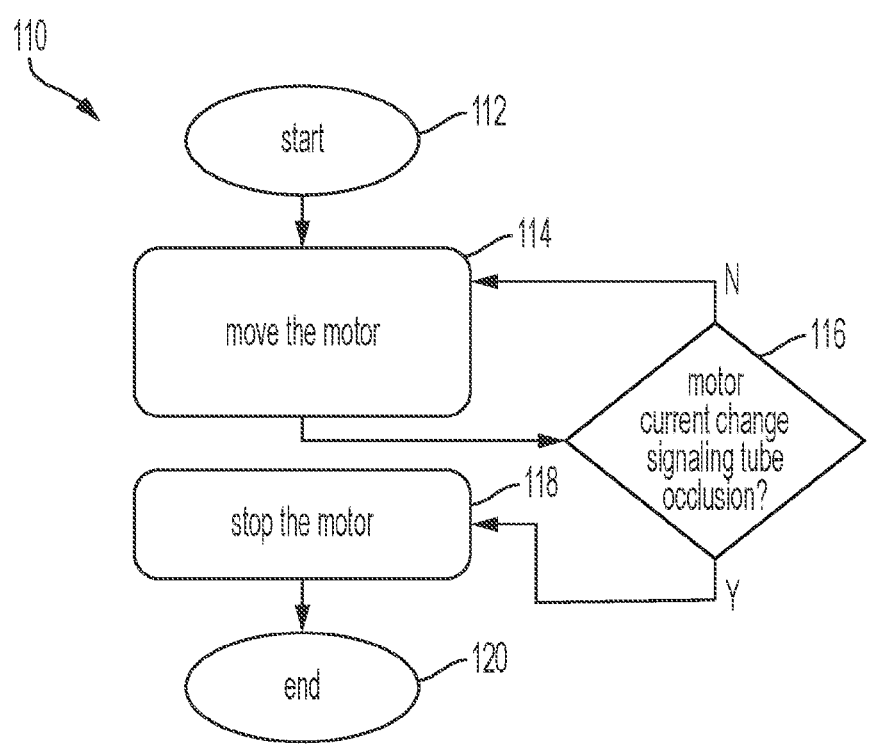
FIG. 5 is a process flow diagram of the structure and method of the present disclosure for occluding a flexible tube using a motorized pinch valve.

FIG. 5 illustrates method 110 of the present disclosure for occluding a flexible tube 16, 42 using a motorized pinch valve 80a, 80b. At oval 112, method 110 begins. At block 114, control unit 60 causes rotary nut motor 82 to rotate and begin to translate threaded shaft 84 and rounded head 86 towards stop 88. At bock 114, control unit 60 also begins to monitor the output of the current sensor 64a, 64b associated with pinch valve 80a, 80b. As discussed above, any current sensor 64a, 64b may be associated with one or more motorized pinch valve 80a, 80b.

At diamond 116, control unit 60 determines if the output from current sensor 64a, 64b shows a spike or characteristic change indicating that tube or line 16, 42 has been fully occluded and that threaded shaft 84 and rounded head 86 are pushing against stop 88, which forces rotary nut motor 82 into a stalled condition. That is, rotary nut motor 82 will draw more current in an end-of-travel, fully occluded state, in an attempt to keep its rotary nut rotating. The additional current draw is detected by current sensor 64a, 64b. If the output from current sensor 64a, 64b at diamond 116 does not show a spike or characteristic change indicating that tube or line 16, 42 has been fully occluded, then method 110 returns to block 114, where control unit 60 continues monitor current sensor 64a, 64b and to cause rotary nut motor 82 to rotate, translating threaded shaft 84 and rounded head 86 towards stop 88. If the output from current sensor 64a, 64b at diamond 116 does show a spike or characteristic change indicating that tube or line 16, 42 has been fully occluded, then method 110 moves to block 118, where control unit 60 causes rotary nut motor 82 to stop. At oval 120, method 110 ends.

Figure 6B:
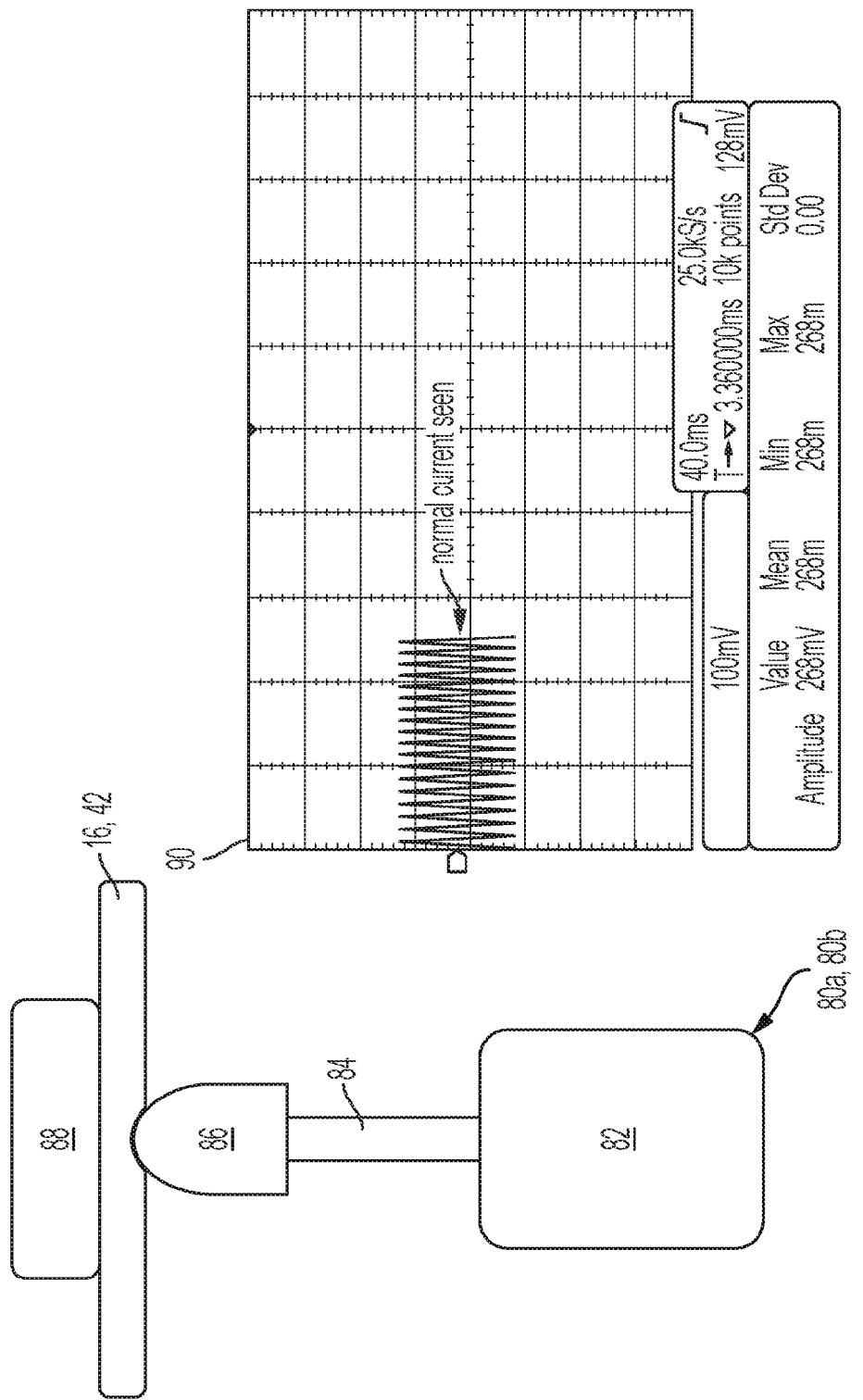

FIGS. 6A to 6D illustrates method 110 in more detail via the sequential display of motorized pinch valve 80a, 80b during occlusion. In FIG. 6A, control unit 60 causes rotary nut motor 82 to be powered and for threaded shaft 84 and rounded head 86 to begin translating. The corresponding output from current sensor 64a, 64b as shown on display 90 indicates that rotary nut motor 82 during the beginning of the occlusion initially draws a normal or expected amount of current. In FIG. 6B, control unit 60 continues to cause rotary nut motor 82 to be powered and for threaded shaft 84 and rounded head 86 to continue translating so as to contact and begin to compress tube or line 16, 42. The corresponding output from current sensor 64a, 64b as shown on display 90 indicates that rotary nut motor 82 during the initial tube contacting portion of the occlusion continues to draw a normal or expected amount of current.

Figure 6C:
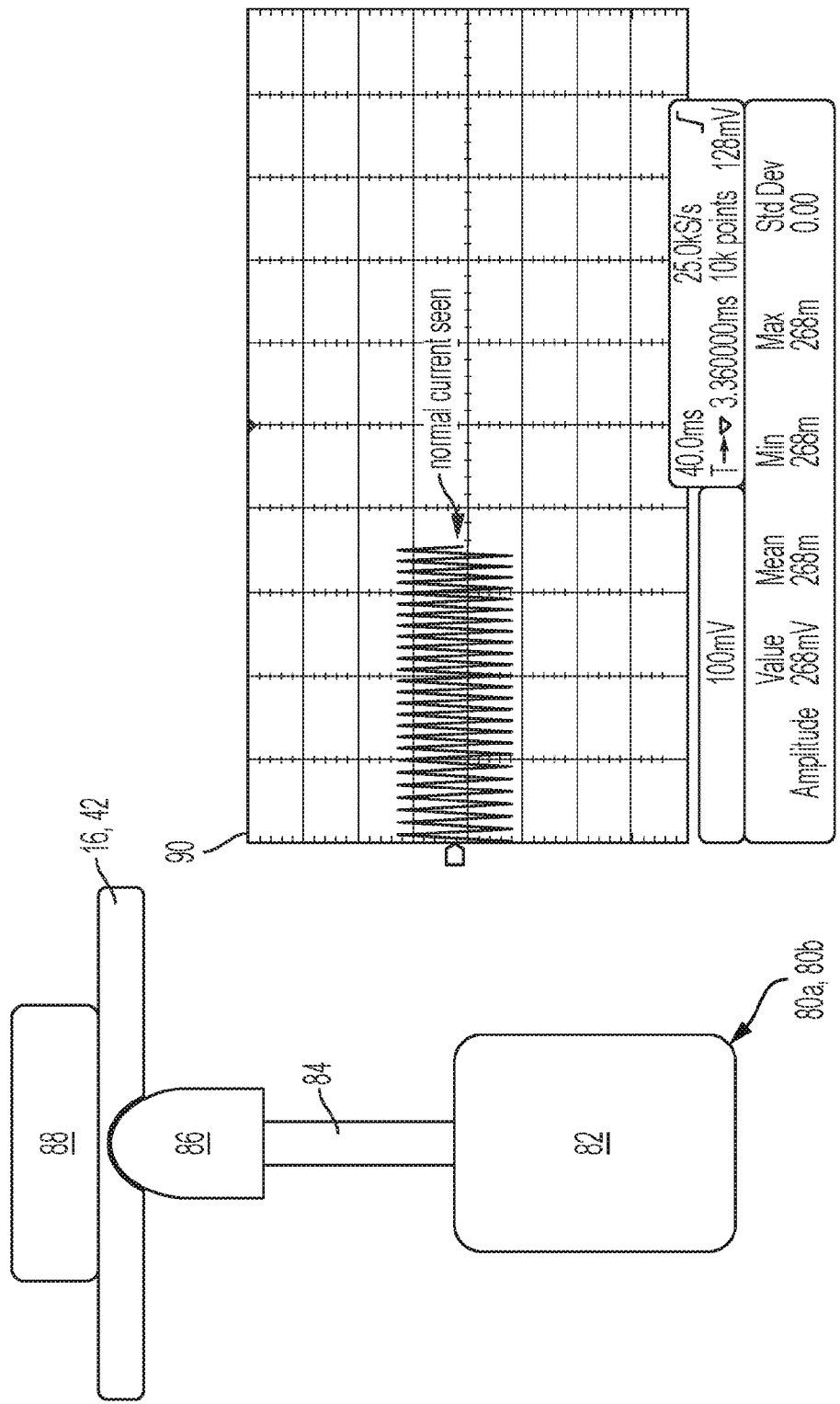
Figure 6D:
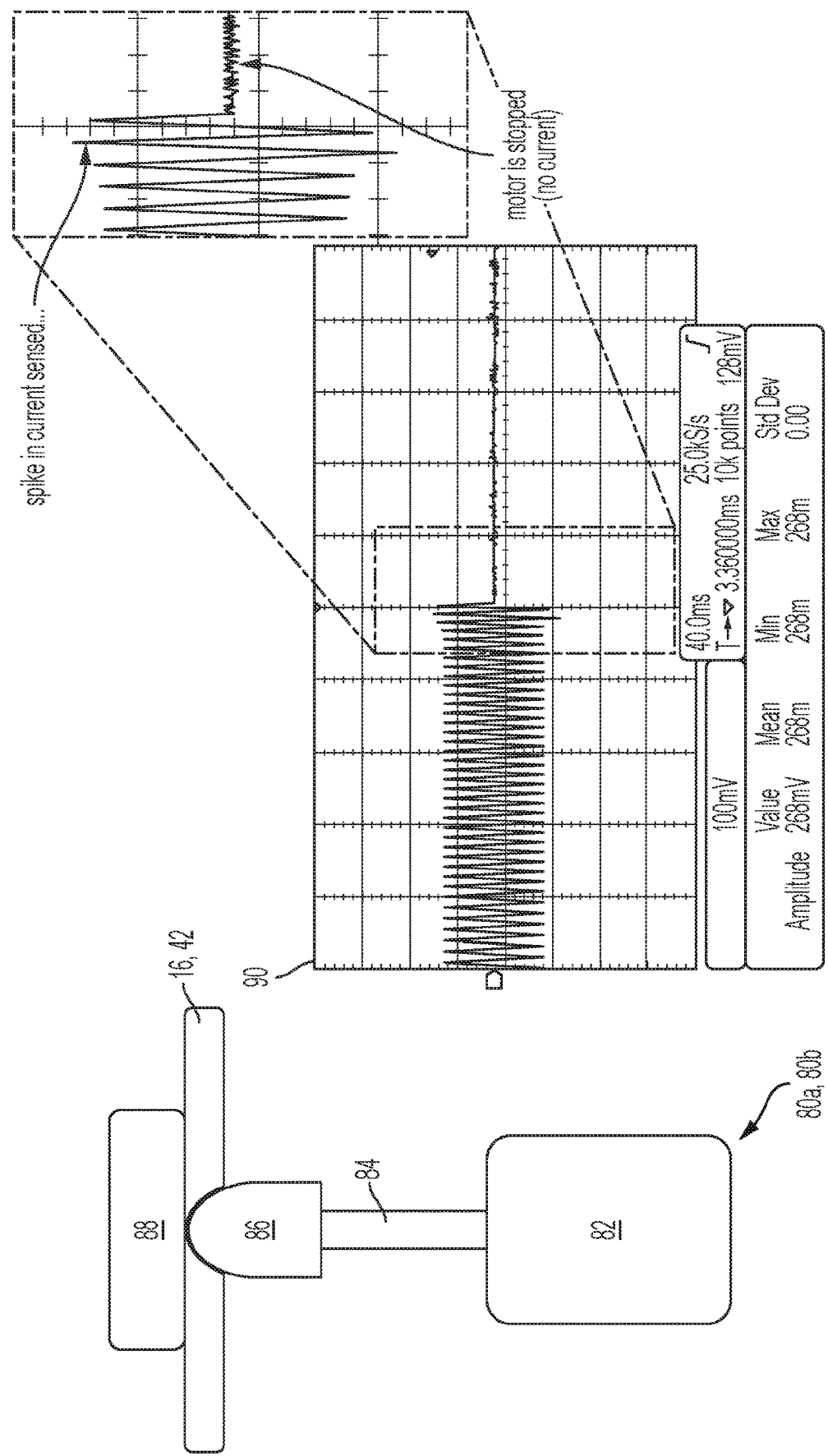

In FIG. 6C, control unit 60 continues to cause rotary nut motor 82 to be powered and for threaded shaft 84 and rounded head 86 to continue translating so as to continue the occlusion of tube or line 16, 42. The corresponding output from current sensor 64a, 64b as shown on display 90 indicates that rotary nut motor 82 during the further tube contacting portion of the occlusion continues to draw a normal or expected amount of current. In FIG. 6D, control unit 60 attempts to continue to cause rotary nut motor 82 to rotate and for threaded shaft 84 and rounded head 86 to continue translating so as to continue the occlusion of tube or line 16, 42. But because tube or line 16, 42 is fully compressed between rounded head 86 and stop 88, the rotary nut can no longer rotate. Rotary nut motor 82 enters a stall condition and draws more current in an attempt to keep the rotary nut rotating. The corresponding output from current sensor 64a, 64b as shown on display 90 detects the additional current draw, indicating that threaded shaft 84 and rounded head 86 have fully occluded tube or line 16, 42, such that head 86 is now pressing against stop 88. Control unit 60 quickly senses the current spike or characteristic increase and cuts power to rotary nut motor 82. Tube or line 16, 42 is fully occluded in FIG. 6D. In an embodiment, control unit 60 is programmed to wait for a period of time, such as about a second, to ensure that the current spike or characteristic increase is due to total tube or line 16, 42 occlusion and not some other current spike anomaly. That is, control unit 60 may cause rotary nut motor 82 to continue to push against tube or line 16, 42 for, e.g., about a second after first seeing the current spike or characteristic increase. Small current spikes not indicating a full occlusion occur typically due to noise. But after seeing the characteristic increase for, e.g., about a second, control unit 60 safely determines a full occlusion of tube or line 16, 42. It should be appreciated however that care is taken to ensure that motor 82 is not powered long enough for it to become heated.

In an embodiment, control unit 60 does not monitor the output from current sensor 64a, 64b in causing the rotary nut motor 82 to rotate in an opposite, tube opening direction. Here, control unit 60 may be programmed to run rotary nut motor 82 in the opposite direction for a determined number of stepper motor steps, or until a limit switch is triggered (e.g., to allow for a less expensive non-stepper motor to be used), wherein it is known that the tip of rounded head 86 is clear from tube or line 16, 42, so that the tube may open fully to allow medical fluid, e.g., PD fluid, to flow therethrough.

FIGS. 5 and 6A to 6D show that the structure and corresponding methodology of motorized pinch valve 80a, 80b the present disclosure successfully occlude tubes or lines 16, 42 regardless of the diameter of the tube (tube 16, 42 has to fit initially in the space between rounded head 86 and stop 88 in FIG. 6A), and regardless of whether the wall thickness of tube 16, 42 varies over time due to repeated occlusion or whether tube 16, 42 has become softer over repeated occlusions in which case tube 16, 42 needs to be compressed more to form a good seal. Successful occlusion of tubes or lines 16, 42 also occurs regardless of manufacturing tolerances.

It should be understood that various changes and modifications to the presently preferred embodiments described herein will be apparent to those skilled in the art. It is therefore intended that such changes and modifications be covered by the appended claims. For example, while system 10 is illustrated as operating with a disposable cassette 70, system 10 may alternatively use durable or reusable components, which are for example disinfected, such as heat disinfected after use. Here, flexible lines or tubes 16, 42 may instead be provided inside PD machine or cycler 20, wherein the lines are disinfected after treatment. Also, while sensors 64a, 64b are described as being current sensors, other types of sensors may be used, such as resistance sensors, hall effect sensors, and current transformers.

The invention is claimed as follows:

1. A medical fluid system comprising:
   a medical fluid pump configured to pump a medical fluid;
   a tube through which the medical fluid pumped by the medical fluid pump flows;
   a pinch valve positioned and arranged to occlude the tube to prevent the medical fluid from flowing through the tube, the pinch valve including a motor;
   a current sensor positioned and arranged to sense a current drawn by the motor of the pinch valve; and
   a control unit operable with the current sensor to monitor the current drawn by the motor while the motor is causing the pinch valve to occlude the tube, the control unit configured to stop the motor when the monitored current indicates an occlusion of the tube.

2. The medical fluid system of claim 1, wherein the monitored current increases to indicate the occlusion of the tube.

3. The medical fluid system of claim 1, wherein the current sensor is provided with the control unit or the pinch valve.

4. The medical fluid system of claim 1, wherein the current sensor is configured to sense the current drawn by multiple motors of multiple pinch valves.

5. The medical fluid system of claim 1, wherein the pinch valve includes a shaft driven by the motor.

6. The medical fluid system of claim 5, wherein the motor is a rotary nut motor and the shaft is a threaded shaft.

7. The medical fluid system of claim 5, wherein the shaft includes a head that contacts the tube, the pitch valve further including a stop against which the head occludes the tube.

8. The medical fluid system of claim 1, wherein the tube is a first tube and the pinch valve is a first pinch valve, and wherein the control unit is operable with the current sensor or a second current sensor to monitor a second current drawn by a second motor of a second pinch valve while the second motor is causing the second pinch valve to occlude the second tube, the control unit further configured to stop the second motor when the monitored second current indicates an occlusion of the second tube.

9. The medical fluid system of claim 1, wherein the control unit is further configured to operate the motor in an opposite direction, without monitoring the current drawn by the motor, to allow the medical fluid to flow through the tube.

10. The medical fluid system of claim 1, wherein the tube is disposable or reusable.

11. The medical fluid system of claim 1, wherein the control unit is configured to wait momentarily after the monitored current initially indicates the occlusion of the tube before stopping the motor.

12. A medical fluid system comprising:
a medical fluid pump configured to pump a medical fluid;
a tube through which the medical fluid pumped by the medical fluid pump flows;
a pinch valve positioned and arranged to occlude the tube to prevent the medical fluid from flowing through the tube, the pinch valve including a motor;
a sensor positioned and arranged to sense a characteristic change associated with the motor of the pinch valve when the tube is occluded; and
a control unit operable with the sensor, the control unit configured to stop the motor when the characteristic change is sensed.

13. The medical fluid system of claim 12, wherein the sensor is a current sensor, a resistance sensor, a hall effect sensor, or a current transformer.

14. The medical fluid system of claim 12, wherein the characteristic change is a characteristic increase in current drawn by the motor.

15. The medical fluid system of claim 12, wherein the control unit is configured to wait momentarily after the characteristic change is sensed before stopping the motor.

* * * * *